United States Patent [19]

McLachlan et al.

[11] Patent Number: 4,768,879
[45] Date of Patent: Sep. 6, 1988

[54] METHOD FOR MEASURING THE SIZE OF OBJECTS IN A FLUID MEDIUM

[75] Inventors: Richard D. McLachlan; Ray W. Chrisman, both of Midland, Mich.

[73] Assignee: The Dow Chemical Company, Midland, Mich.

[21] Appl. No.: 875,168

[22] Filed: Jun. 17, 1986

[51] Int. Cl.⁴ .................. G01N 21/64; G01N 21/65; G01N 15/02
[52] U.S. Cl. .................................. 356/301; 356/318; 356/335; 250/459.1
[58] Field of Search ............... 250/458.1, 461.1, 365, 250/461.2, 459.1; 356/336, 301, 317, 318, 417, 335

[56] References Cited

U.S. PATENT DOCUMENTS

| | | | |
|---|---|---|---|
| 3,887,812 | 6/1975 | Hirschfeld | 250/458.1 |
| 4,408,880 | 10/1983 | Tsuj et al. | 356/338 |
| 4,573,761 | 3/1986 | McLachlan | 356/301 |

FOREIGN PATENT DOCUMENTS 2571144 4/1986 France .............................. 356/301

OTHER PUBLICATIONS

Journal of Polymer Science, pt. C, "Particle Size Distribution by Flow Ultramicroscopy", Davidson et al., pp. 235-255, 1971, No. 35.

Primary Examiner—F. L. Evans
Attorney, Agent, or Firm—Leorman & McCulloch

[57] ABSTRACT

A method for determining the size of moving objects present in a transparent or translucent fluid medium comprises illuminating a zone of the suspension with monochromatic light, collecting scattered light having a wavelength characteristic of the objects or of the medium, and measuring the intensity and variations in intensity of the collected light. The data thus obtained may be compared with data obtained from corresponding measurements of corresponding mediums containing corresponding objects of known size.

17 Claims, 2 Drawing Sheets

TABLE 1

KNOWN AND MEASURED PARTICLE SIZES FOR
POLYSTYRENE BEADS OF VARIOUS DIAMETERS

| KNOWN DIAMETER (MICRONS) | $\left(\dfrac{V_x - X}{X}\right)^{1/3}$ | MEASURED DIAMETER (MICRONS) |
|---|---|---|
| 153 | .81 | 152 |
| 174 | .93 | 175 |
| 201 | 1.20 | 225 |
| 244 | 1.20 | 225 |
| 301 | 1.54 | 289 |
| 374 | 1.96 | 368 |
| 447 | 2.44 | 459 |

*Fig. 3*

TABLE 2

MEASURED PARTICLE DIAMETERS FOR 447 MICRON
POLYSTYRENE BEADS IN SUSPENSIONS OF
VARIOUS CONCENTRATIONS

| CONCENTRATION (WEIGHT PERCENT) | $\left(\dfrac{V_x - X}{X}\right)^{1/3}$ | MEASURED DIAMETER (MICRONS) |
|---|---|---|
| 48.5 | 2.26 | 425 |
| 41.4 | 2.24 | 421 |
| 36.1 | 2.31 | 433 |
| 32.0 | 2.34 | 440 |
| 28.8 | 2.34 | 439 |
| 23.9 | 2.34 | 440 |

*Fig. 4*

METHOD FOR MEASURING THE SIZE OF OBJECTS IN A FLUID MEDIUM

This invention relates to the spectroscopic measurement of the size of discrete particles, droplets, or gas bubbles, in motion in a fluid medium.

BACKGROUND OF THE INVENTION

Many commercial chemical processes rely upon suspending solid particles in a fluid, or combining two or more immiscible fluids in such manner that one forms as droplets or gas bubbles suspended in the other.

The particles, droplets, or gas bubbles (hereinafter sometimes referred to as "objects" for convenience) then undergo some reaction or physical change, such as polymerization, the success of which is dependent upon the sizes of the objects in suspension. If the sizes of the objects can be measured in-situ, adjustments can be made in a process during the progress thereof to optimize the resulting product. However, in-situ measurement of the size of objects may not always be possible or convenient by conventional means. For example, in processes wherein a medium includes liquid droplets or bubbles whose size is critical to the product produced from such process, measurement of the size often requires the removal of a sample of the medium from the reaction or mixing vessel. However, it is difficult, or impossible, to remove and analyze such a sample without causing a change in the droplet or bubble size.

In the absence of suitable methods for in-situ measurements of the sizes of objects, it is not uncommon for adjustments in a process to be made on an empirical basis. The necessity of relying upon empirical techniques is inherently wasteful of both time and materials, and unduly increases production costs.

An object of the present invention, therefore, is to provide a method for the direct, in-situ measurement of the sizes of objects present in a fluid medium and thus improve production efficiencies by eliminating some empirical adjustments.

A co-pending application, U.S. Ser. No. 756,359, now abandoned, of the same assignee discloses a method for in-situ determination of the sizes of objects, present in a fluid medium and is based on measuring the intensity and variance in intensity of light reflected from such objects. In that method the intensity of the reflected light depends on the refractive index of the medium containing the objects. Therefore, successful application of such method requires that the refractive index of the medium remain substantially constant during the measurements.

The present method comprises the measurement of the intensity and variance of light scattered by particles, droplets, or bubbles present in a transparent or translucent fluid medium. References hereinafter to scattered light include Raman scattered light and light absorbed by and reemitted from objects or liquids at a frequency different from that of the illuminating light.

One of the differences between the method of this invention and that disclosed in the above mentioned co-pending application is that scattered light is not affected to any substantial degree by changes in the refractive index of the medium. Thus, the present method is applicable in those instances in which the refractive index of the medium is variable.

Another advantage of the present method is that it enables the measurements to be restricted to the light scattered by specific substances only, whereas the reflected light method disclosed in the aforementioned application measures light reflected from all particulate matter in the sample. Thus, by using the method of the present invention it is possible to measure the size of objects of a specific chemical composition in a medium containing other materials of different compositions, provided the other materials do not severely affect the transmission of the illuminating light and the scattered light.

SUMMARY OF THE INVENTION

The present invention comprises a method of measuring in-situ the size of objects present in a flowing, stirred, or agitated translucent or transparent fluid medium, and includes the following steps:
a. illuminating a small zone of the suspension with monochromatic light;
b. collecting light scattered by objects traversing the illuminated zone at a wavelength characteristic of molecules present in such objects, or characteristic of the molecules present in the fluid medium;
c. determining both the average intensity and the variation in the intensity of the collected light over a period of time; and
d. comparing the data obtained from such measurements with values obtained in the same manner from corresponding suspensions containing objects of known size.

THE DRAWINGS

Apparatus adapted for use in performing the method according to the invention is illustrated in the accompanying drawings wherein:

FIG. 3 is a table comparing the sizes of objects measured according to the invention with the actual sizes thereof; and FIG. 4 is a table illustrating the absence of significant effects due to variations in the concentration of objects whose size is measured according to the invention.

DETAILED DESCRIPTION OF THE INVENTION

Figure 1:
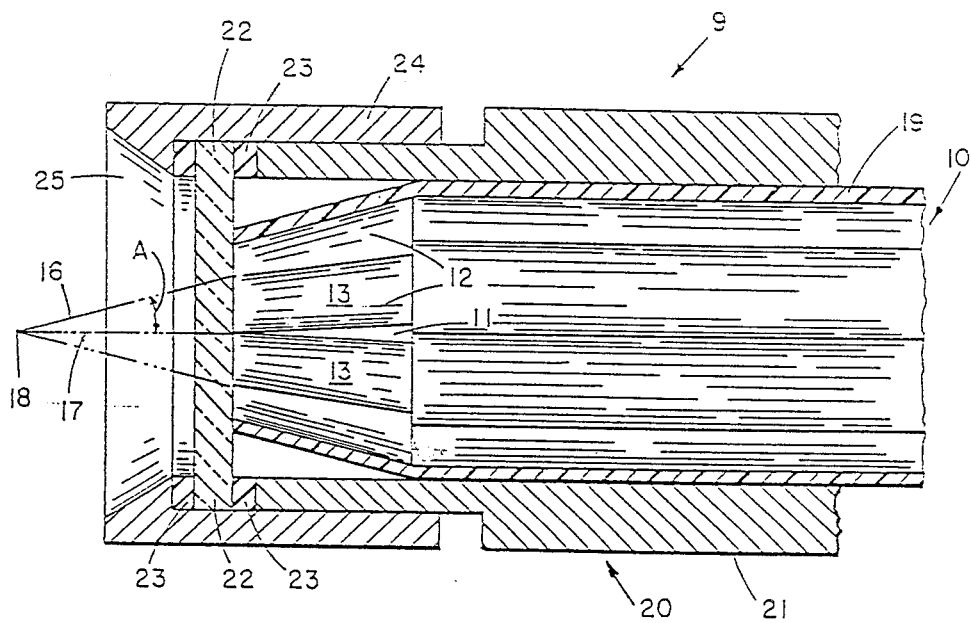
FIG. 1 is a fragmentary, isometric, partly sectional view of a fiber optic probe for illuminating a medium containing light scattering objects and collecting scattered light.

The method according to the preferred embodiment of the invention relies upon the phenomenon that, when a transparent or translucent fluid medium containing objects such as immiscible liquid droplets, or gas bubbles, or solid particles, is illuminated by monochromatic light, the light scattered by such objects has a wavelength corresponding to that of the illuminating light and, in addition, small amounts of light having wavelengths other than that of the illuminating light. In those instances in which the other wavelengths differ from that of the illuminating light by amounts corresponding to vibrational frequencies of the molecules of the objects in the medium, the phenomenon is known as the Raman effect, whereas in those instances in which the other wavelengths differ from that of the illuminating light by an amount corresponding to electronic transitions of the molecules of the objects in the medium the phenomenon is known as fluorescence.

The amount of light scattered at a particular wavelength is proportional to the intensity of the illuminating light and the concentration of molecules which scatter light of such wavelength. If two or more different kinds of materials are present in the medium, each may scatter its own characteristic frequencies at an intensity proportional to the relative concentrations of the materials. If the different materials are present in separate phases, the relative intensity of the light scattered by each phase is proportional to the volume fraction occupied by that phase and the intensity of the illuminating light within that phase.

The presence of a single object, such as a solid particle, droplet of liquid, or gas bubble, in a zone of a transparent or translucent fluid medium illuminated with monochromatic light will enable the production of a scattered light signal which is proportional to the volume of the object. If the medium contains a plurality of such objects, the signal will be approximately proportional to the total volume of the objects (i.e., volume fraction) present in the sampled zone. If the objects are not stationary, but continually traverse the illuminated zone of the medium, the intensity of the signal produced will vary with the statistical variation in the number and positions of the objects in the zone. Thus, for a flowing or stirred transparent or translucent fluid medium containing the objects, the average intensity of the signal due to the objects is approximately proportional to its volume fraction, and the variation in the intensity (variance) of such signal due to motion of the objects is approximately proportional to the volumes of the individual objects.

In addition to variance due to motion of the objects in the medium, the scattered light signal also contains statistical (photon) variance which is equal to the average (mean) intensity. An approximation of the relationship between the intensity and variance in the signal and the average volume of the objects is expressed by the following equation:

$$V \alpha \left( \frac{V_x - X}{X} \right) \quad \text{[Equation 1]}$$

where V is the average volume of the objects and X and $V_x$ are the mean intensity and the variance, respectively, of the collected scattered light. The expression for the diameter (D) of the objects thus is:

$$D = K \left( \frac{V_x - X}{x} \right)^{\frac{1}{3}} \quad \text{[Equation 2]}$$

where K is a quantity whose value depends on the particular Raman or fluorescence wavelength measured, the intensity of the illuminating light, the geometry of the measuring device, and the efficiency of the light measuring system. K thus is a constant for a particular combination of object material, wavelengths of the illuminating and scattered lights, optical system, and photometer. The value of K can be determined by measuring the intensity and variance of the collected scattered light from a medium containing objects of known size and composition. The size of objects of unknown size in an otherwise corresponding medium can be determined by repeating the measurements, using the corresponding medium and the same apparatus, and applying Equation 2.

The method is also applicable to cases in which objects are present in Raman scattering liquid mediums. Examples of these instances include gas bubbles or water droplets in organic liquids. The presence of such objects in the illuminated zone will reduce the intensity of the Raman signal from the liquid medium by an amount proportional to their volumes. The reduction in intensity, and thus the intensity itself, will vary with the statistical variation in the number and position of these objects in the illuminated zone. The average volume of these objects can be determined by application of Equation 2.

In many commercial processes precise quantitative measurement of the size of objects is not required; it is sufficient to ascertain whether or not the size is within acceptable limits. In these cases the use of calibration mediums containing objects of known size is unnecessary, because analyses of particular mediums containing objects of acceptable size will make it possible for an analyst experienced in analyzing such medium to determine from values obtained from the mean and variance of the scattered light intensity of a medium whether or not the size of the objects is within acceptable limits.

Figure 2:
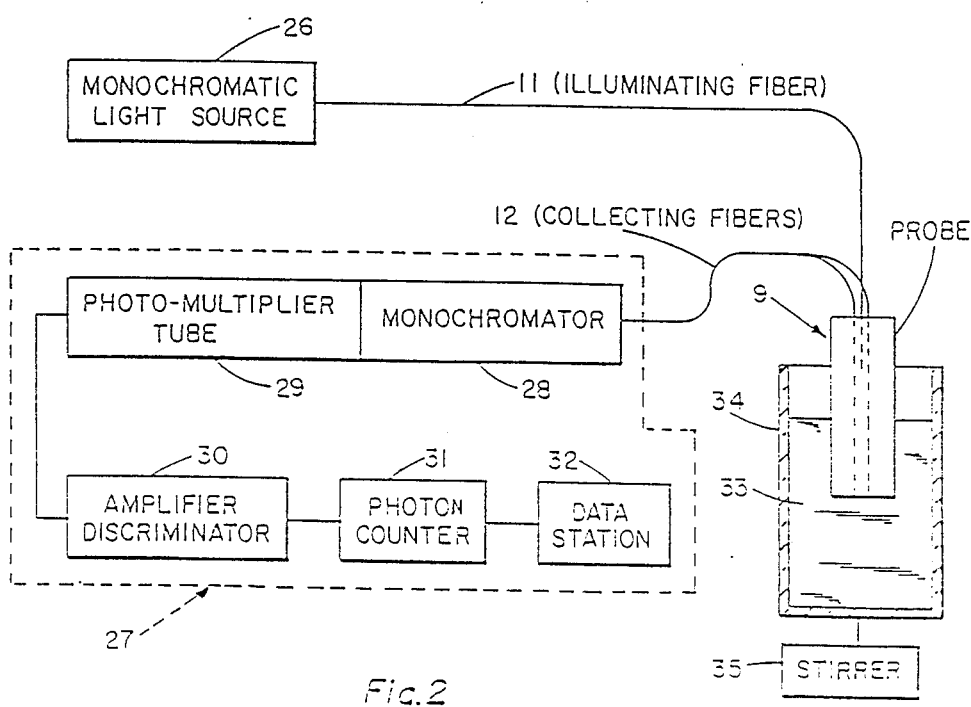
FIG. 2 is a diagrammatic illustration of an operative system.

Apparatus adapted for use in the process according to the invention is illustrated in FIGS. 1 and 2 and comprises a probe 9 such as that disclosed in U.S. Pat. No. 4,573,761. The probe includes a bundle 10 of optical fibers having a central illuminating fiber 11 encircled by a plurality of light collecting fibers 12. Each fiber has a transparent core formed of silica or other suitable material encased in a transparent jacket 13 having a refractive index lower than that of the core. The diameter of each core preferably is uniform and within the range of between about 200 and 700 microns, with a diameter of about 600 microns being preferred. Preferably, the jacket 13 of each fiber is removed adjacent corresponding ends of the fibers, thereby enabling the longitudinal axes 16 of such ends of the light collecting fibers to converge in a direction beyond the ends of the fibers and intersect the longitudinal axis 17 of the illuminating fiber 11 at a common point 18 located externally of the probe. Preferably, the angle A between the axes 16 and 17 is between about 10° and 20°.

The bundle 10 of fibers is encircled by an opaque, heat shrinkable tube 19 that maintains the bundle of fibers in assembled relation, and the entire assembly is fitted into a fluid tight housing 20 having a tubular body 21 provided with a transparent window 22 at one end that is confronted by the free ends of the fibers 11 and 12. The window is flanked by seals 23 and the window and seals are maintained assembled with the body 21 by a cap 24 having a flanged opening 25 in axial alignment with the body. The cap and the body preferably are correspondingly threaded.

The materials from which the body, the cap, the seals, and the window are formed may vary, but should be such as to enable the probe to be immersed in the fluid medium that is to be analyzed without adverse effects on the probe or the medium.

FIG. 2 illustrates a typical arrangement of components for use in the performance of the process. The illuminating fiber 11 extends outwardly of the probe 9 and is coupled to a suitable monochromatic light source 26. The light collecting fibers 12 also extend outwardly of the probe and are coupled to a spectrophotometer 27 including a monochromator 28 which filters and passes light of a selected wavelength. A photomultiplier tube 29 produces electrical pulses which are amplified by an amplifier/discriminator 30. The amplified pulses are counted by a photon counter 31 and the resulting data passed to a data station 32 at which the measurement calculations are made.

Although the individual components of the system may be varied as required to enable the method to be practiced efficiently, satisfactory results have been obtained by using as the light source a Lexel Model 95-4 continuous wave argon ion laser having an output of 1.5 W at 514.5 nm, a Jobin-Yvon HR-320 monochromator, a Hamamatsu R 955 photomultiplier tube in a Products for Research Model TE 177 thermoelectric refrigerated chamber, a Princeton Applied Research (PAR) Model 1121A amplifier/discriminator, a PAR Model 1109 photon counter, and a Perkin-Elmer Model 3600 infrared data station.

In use the probe is immersed in a transparent or translucent fluid medium 33 having liquid droplets, gas bubbles, or solid particles present therein. The medium is contained in a suitable vessel 34 with which is associated a magnetic stirrer 35 or other suitable mechanism for setting the objects in motion. Light transmitted by the illuminating fiber will illuminate a small zone of the medium adjacent the window 22. As objects continually traverse the illuminated zone they will be illuminated. Light scattered by the illuminated objects will be collected by the fibers 12 and transmitted to the spectrophotometer 27.

ILLUSTRATIVE EXAMPLE

Seven samples were prepared from groups of monosized polystyrene beads having known diameters ranging from 153 microns to 447 microns. Each sample contained 10 grams of the same size beads suspended in 15 milliliters of clear water and was stirred with a magnetic stirrer. The probe 9, connected to the monochromatic light source and the spectrophotometer 27 as shown in FIG. 2, was immersed in each sample and the intensity and variations in intensity of the scattered light at 542.5 nm (a difference of 1002 cm$^{-1}$ from the 514.5 nm wavelength of the illuminating light) due to the strongest Raman line of polystyrene, were determined by counting the pulse signals for 2000 two-millisecond intervals with a delay of fifty milliseconds between intervals. The mean intensity and the variance of each data set were computed by the data station.

The correlation between the known particle diameters and the function of the average (mean) intensity and variance of the Raman scattered light, i.e., the right-hand side of Equation 2, was computed by the method of least squares. The diameters were then calculated by application of the resulting linear regression equation:

$$D = A\left(\frac{V_x - X}{X}\right)^{\frac{1}{2}} + B \quad \text{[Equation 3]}$$

where A and B are constants resulting from the least squares linear regression. These data and results are shown in Table 1 (FIG. 3).

The effect of object concentration on the measured object diameter was determined by repeating the measurements with six additional suspensions each containing 447 micron diameter beads at concentrations ranging from about 24% to 48.5% by weight. The results of these measurements are tabulated in Table 2 (FIG. 4). The variations in measured size due to variations in concentration are slight; the measured size for all concentrations being within 5% of the known size.

What is claimed is:

1. An in-situ method for determining the size of objects present and moving in a translucent or transparent fluid medium comprising:
   a. illuminating with monochromatic light a zone of said medium traversed by said objects;
   b. collecting light scattered selectively by said objects or said medium and having a wavelength that is characteristic of the composition of said objects or said medium;
   c. measuring a selected plurality of times the intensity of the collected light over a plurality of spaced intervals of time;
   d. calculating the mean intensity and the variance in the intensities of the scattered light collected during said time intervals; and
   e. comparing data obtained from such measurements and calculations with values obtained from the making of corresponding measurements and calculations of corresponding objects present and moving in a corresponding medium.

2. The method according to claim 1 including transmitting the light to said zone by optical fiber means.

3. The method according to claim 1 including collecting the scattered light by optical fiber means.

4. The method according to claim 1 including illuminating said zone and collecting the scattered light by means of a probe immersed in said medium, said probe having therein means for transmitting the illuminating light and means for transmitting the collected scattered light.

5. The method according to claim 1 including illuminating said zone by light emitted from a continuous wave gas laser.

6. The method according to claim 1 including measuring the intenstiy of said collected light by spectrophotometer means.

7. The method of claim 1 including filtering the collected light prior to measuring the intensity and to limit the light utilized for such measurements to that having said wavelength.

8. The method according to claim 1 wherein said objects comprise solid particles.

9. The method according to claim 1 wherein said objects comprise liquid droplets.

10. The method according to claim 1 wherein said objects comprise gas bubbles.

11. The method according to claim 1 wherein the illuminating light is scattered due to the Raman effect.

12. The method according to claim 1 wherein the illuminating light is scattered due to fluorescence.

13. The method according to claim 1 wherein the intervals of time are of substantially uniform duration.

14. The method according to claim 13 wherein the space between successive intervals is substantially uniform.

15. An in-situ method for determining the size of objects present and moving in a translucent or transparent fluid medium comprising:
   a. illuminating with monochromatic light a zone of said medium traversed by said objects;
   b. collecting light scattered selectively by said objects or said medium and having a wavelength that is characteristic of the composition of said objects or said medium;

c. measuring a selected plurality of times the intensity of the collected light over a plurality of spaced intervals of time;
d. calculating the mean intensity and the variance in intensities of the scattered light collected during said intervals of time; and
e. comparing the measured intensity and variance thereof with calibration data obtained by performing the above steps a-d using corresponding objects of known size present and moving in a corresponding fluid medium.

16. The method according to claim 16 wherein the intervals of time are of substantially uniform duration.

17. The method according to claim 16 wherein the space between successive intervals is substantially uniform.

* * * * *